US009848862B2

United States Patent
Bass et al.

(10) Patent No.: US 9,848,862 B2
(45) Date of Patent: Dec. 26, 2017

(54) RETRACTOR BLADE ASSEMBLY

(71) Applicant: TEDAN SURGICAL INNOVATIONS, LLC., Sugarland, TX (US)

(72) Inventors: Daniel Bass, Half Moon Bay, CA (US); Thomas T. Terramani, Glendale, CA (US); Adam B. Young, Redwood City, CA (US)

(73) Assignee: Tedan Surgical Innovations, LLC., Sugar Land, TX (US)

( * ) Notice: Subject to any disclaimer, the term of this patent is extended or adjusted under 35 U.S.C. 154(b) by 468 days.

(21) Appl. No.: 14/678,344

(22) Filed: Apr. 3, 2015

(65) Prior Publication Data

US 2016/0287234 A1    Oct. 6, 2016

(51) Int. Cl.
  *A61B 17/02* (2006.01)
  *A61B 1/32* (2006.01)
  *A61B 17/00* (2006.01)

(52) U.S. Cl.
  CPC ........... *A61B 17/02* (2013.01); *A61B 1/32* (2013.01); *A61B 17/0206* (2013.01); *A61B 17/0218* (2013.01); *A61B 17/0293* (2013.01); *A61B 2017/00473* (2013.01); *A61B 2017/00477* (2013.01)

(58) Field of Classification Search
  CPC .......... A61M 29/00; A61B 1/32; A61B 17/02; A61B 17/0206; A61B 17/0218; A61B 17/025; A61B 17/0281; A61B 17/0293; A61B 17/44; A61B 2017/0256
  See application file for complete search history.

(56) References Cited

U.S. PATENT DOCUMENTS

| 569,839 | A | * | 10/1896 | Roeloffs | A61B 17/02 600/213 |
|---|---|---|---|---|---|
| 4,971,038 | A | | 11/1990 | Farley | |
| 5,882,298 | A | | 3/1999 | Sharratt | |
| 5,902,233 | A | | 5/1999 | Farley et al. | |
| 5,984,865 | A | | 11/1999 | Farley et al. | |
| 5,984,867 | A | * | 11/1999 | Deckman | A61B 17/0206 600/231 |
| 6,042,540 | A | | 3/2000 | Johnston et al. | |

(Continued)

OTHER PUBLICATIONS

"International Search Report for International Application No. PCT/US16/23409 dated Jun. 10, 2016".

*Primary Examiner* — Kevin T Truong
*Assistant Examiner* — Tracy Kamikawa
(74) *Attorney, Agent, or Firm* — Kramer Amado, P.C.

(57) ABSTRACT

A retractor blade assembly includes an arm member, blade connector and a retractor blade having stem member provided at the top of the blade. The stem member includes a first pin member, provided at an upper portion of the stem member. The first pin member has at least one abutment extending outward from the stem member, a first groove provided below the first pin member, a second groove provided below the first groove, provided about the circumference of the stem member, a second pin member having at least one abutment extending from the second groove. The blade connector cooperatively engages the stem member permitting the retractor blade to operate in a rotatable mode and a locked mode.

20 Claims, 5 Drawing Sheets (56) References Cited

U.S. PATENT DOCUMENTS

| | | | |
|---|---|---|---|
| 6,206,828 B1 * | 3/2001 | Wright | A61B 17/0206 600/232 |
| 6,860,850 B2 | 3/2005 | Phillips et al. | |
| 7,473,223 B2 | 1/2009 | Fetzer | |
| 7,569,014 B2 | 8/2009 | Bass et al. | |
| 7,588,537 B2 | 9/2009 | Bass | |
| 8,257,255 B2 | 9/2012 | Farley et al. | |
| 8,360,971 B2 | 1/2013 | Farley et al. | |
| 8,900,137 B1 | 12/2014 | Lovell et al. | |
| 8,974,381 B1 * | 3/2015 | Lovell | A61B 90/30 600/215 |
| 2011/0201897 A1 | 8/2011 | Bertagnoli et al. | |
| 2012/0088979 A1 | 4/2012 | Nunley et al. | |
| 2014/0031874 A1 * | 1/2014 | Kucharzyk | A61B 17/7076 606/279 |
| 2014/0066718 A1 | 3/2014 | Fiechter et al. | |

* cited by examiner

RETRACTOR BLADE ASSEMBLY

TECHNICAL FIELD

The invention relates to a retractor blade assembly. More particularly, the invention relates to a retractor blade assembly having a connector and retractor blade and pin member configuration for facilitating use in both a locked mode and an unlocked swivel mode.

BACKGROUND

Surgical procedures often require the creation of a surgical exposure to allow a surgeon to reach deeper regions of the body. The surgical exposure is usually started with an incision of a suitable depth. Surgical instruments known as retractors are then inserted into the incision and used to pull back skin, muscle and other soft tissue to permit access to the desired area.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat and may have end prongs of various configurations to make it easier to pull back tissue. The retractor blades may be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

Most retractors do not have the versatility to provide an easy to use mechanism that permits the user to lock the retractor blade between an unlocked mode and locked mode.

SUMMARY

In light of the present need for retractor assembly capable of being operated in a locked mode and an unlocked mode, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

The retractor blade assembly includes an arm member and a retractor blade having stem member provided at the top of the blade. The stem member including a first pin member, provided at an upper portion of the stem member, having at least one abutment extending outward from the stem member. The stem member further includes a first groove provided below the first pin member, provided about the circumference of the stem member. The stem member further includes a second groove provided below the first groove, provided about the circumference of the stem member, and a second pin member having at least one abutment extending from the second groove.

The retractor blade assembly further includes a blade connector including a body including a first aperture and at least one notch, extending from a top surface of the body through a bottom surface of the body and configured to receive insertion of the stem member therein. The blade connector further includes a second aperture extending from a side wall into the interior of the body in communication with the first aperture, and a locking assembly provided in the second aperture configured to selectively engage the first groove and the second groove of the stem member in an inserted position.

When the stem member of the retractor blade is inserted in the first aperture in a first position, the locking assembly engages the first groove of the stem member. The first pin member is located above the top surface of the blade connector and the second pin is located below the bottom surface of the blade connector, permitting the stem member and connected retractor blade to rotate.

When the stem member of the retractor blade is in a second position, the locking assembly engages the second groove of the stem member preventing vertical movement of the stem member, and at least one of the abutments of the second pin member is located in at least one of the notches of the blade connector, thereby locking the blade member in a locked position.

In an embodiment of the retractor blade assembly, the stem member is in an inserted position with the blade connector, the abutment of first pin member permits removal of the stem member from the blade connector when aligned with at least one notch of the blade connector and prevents removal of the stem member when misaligned aligned.

BRIEF DESCRIPTION OF THE DRAWINGS

In order to better understand various embodiments, reference is made to the accompanying drawings, wherein.

To facilitate understanding, identical reference numerals have been used to designate elements having substantially the same or similar structure and/or substantially the same or similar function.

DETAILED DESCRIPTION

When operating a retractor assembly, the ability to easily lock a retractor blade in a selected position, and also easily unlock the retractor blade permitting free movement, is invaluable for a user that needs multi-functional operation. As discussed, most retractor blade assemblies do not provide the capability of easily unlocking and locking the retractor blade at a selected angle. Accordingly, it is desirable to provide a retractor assembly that has a connection that permits the retractor blade to be unlocked and locked at a selected angle.

The foregoing advantages of the invention are illustrative of those that can be achieved by the various embodiments and are not intended to be exhaustive or limiting of the possible advantages which can be realized. Thus, these and other advantages of the various embodiments will be apparent from the description herein or can be learned from practicing the various embodiments, both as embodied herein or as modified in view of any variation that may be apparent to those skilled in the art. Accordingly, the present invention resides in the novel methods, arrangements, combinations, and improvements herein shown and described in various-embodiments.

Referring now to the drawings, wherein the illustrations are for purposes of describing one or more embodiments and not for the purposes of limiting the same, referring now to FIGS. 1-5, the retractor blade assembly 10 generally includes a retractor arm 14, a blade connector 16 having an aperture 32 and one or more notches 34a, 34b extending through the connector 16. The blade connector 16 is operatively connected to the retractor arm 14, and the retractor blade 12 is removably connected to the blade connector 16, and is capable of being selectively moved by a user between a rotatable swivel mode and a locked mode.

Figures 1, 2A, 2B:
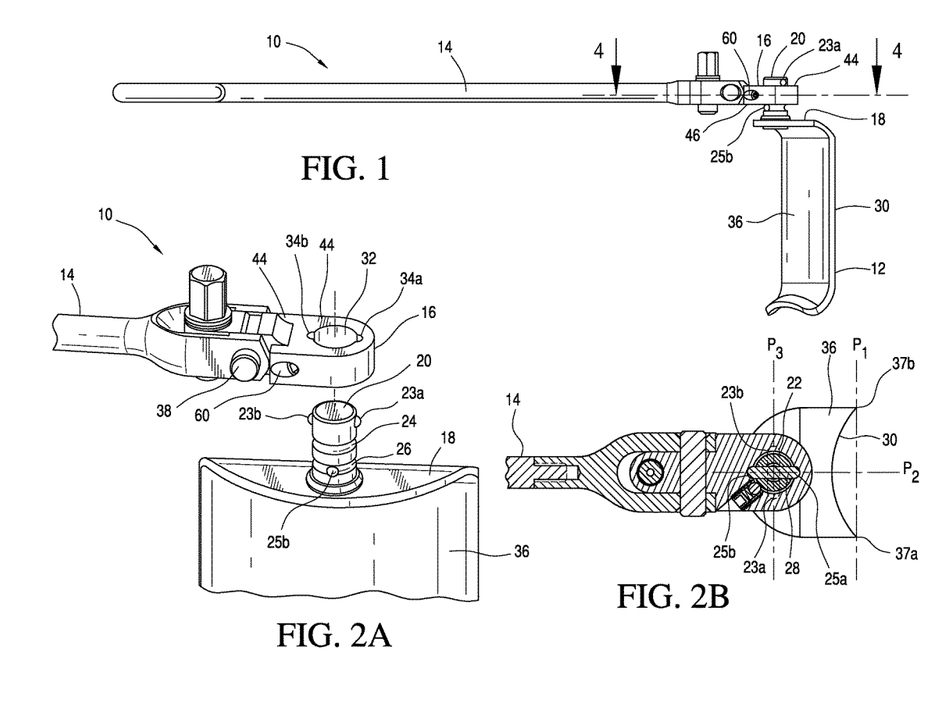
FIG. 1 is a side perspective view of a retractor blade assembly with a retractor blade in an unlocked rotatable mode.
FIG. 2A is an exploded top perspective view of the retractor blade assembly of FIG. 1 illustrating the connection between a blade connector and the retractor blade.
FIG. 2B is a top sectional view of the retractor blade of FIG. 1, illustrating the offset relationship of a first pin member and a second pin member.

As shown in FIG. 2, the retractor blade 12 generally includes a stem member 20, which extends in a generally upward direction from a generally top portion 18 of the retractor blade 12. The stem member 20 is configured to facilitate locking and rotatable engagement of the retractor blade 12 with the connector 16. As depicted, the stem member 20 may have a generally cylindrical body 42 to facilitate rotation of retractor blade 12 relative to the blade connector 16. However, notably, it is contemplated that the body 42 may have a variety of shapes, sizes and dimensions to facilitate locking engagement, as well as, rotatable or slidable movement with respect to the blade connector 16.

The stem member 20 further includes a first pin member 22, provided at a generally upper or top portion of the stem member 20. As shown, the first pin member 22 may include one or more abutments 23a, 23b, adapted for locking engagement with the first aperture 32 and respective notches 34a and 34b formed in the blade connector 16, which will be further described later herein.

In the embodiment shown in FIGS. 2A-4, the first pin member 22 provides dual abutment members 23a, 23b. Notably, it is contemplated that the retractor assembly 10 may function with the first pin member 22 having a singular abutment member 23, as well as more than two abutment members 23, for facilitating operative engagement with the first aperture 32 and notches 34a, 34b of the blade connector 16.

As shown, the stem member 20 may further include a first groove 24 or top groove, formed on the stem member 20 generally below the first pin member 22. The first groove 24 is generally formed around the circumference of the stem member 20, providing a cut-out surface to receivably engage components provided in the interior of the blade connector 16.

The stem member 20 further includes a second groove 26 or bottom groove portion, spaced generally below the first groove 24. The second groove 26 is provided around the circumference of the stem member 20, and is also configured to receivably engage components provided in the interior of the blade connector 16, when the stem member 20 is inserted in the blade connector 16. As shown, mounted within the second groove 26, the stem member 20 includes a second pin member 28, extending generally outward therefrom. The second pin member 28 generally includes one or more abutments 25a, 25b, which extend in generally opposing directions, and are configured for operative engagement with the aperture 32 and notches 34a, 34 of the blade connector 16 to lock the retractor blade 12 at a selected position or angle relative to the locking arm 14.

As shown in FIG. 2B, the retractor blade 12 includes a first portion 30, an opposing second portion 36 and a top portion 18. The second portion 36 has outer edges 37a, 37b which define a plane $P_1$. One of the abutments 25b of the second pin member 28 extend generally outward from the body 42 perpendicular to the plane $P_1$. The abutment 25b on generally the same side of the second portion 36 of the retractor blade 12. The opposing abutment 25a extends generally outward from the body 42 in an opposite direction from the body 42, outward from the first portion 30 of the retractor blade 12.

As illustrated in FIGS. 2A and 2B, the first pin member 22 and abutment 23a and second pin member 28 and abutment 25a are offset from each other about the circumference of the stem member 20 by approximately 90 degrees. The first pin member 22 and abutment 23a define a plane $P_2$ which is parallel to the plane $P_1$, and as such the first pin member and respective abutments are parallel to the plane $P_1$. It is contemplated that the first pin member 22 and second pin member 28 may individually and/or collectively be configured at different selected locations on the stem member 20, to facilitate locking engagement of the retractor blade 12 with the blade connector 16 aperture 32 and respective notches 34a, 34b at various positions.

As illustrated, the blade connector 16 is provided generally at an end portion of the retractor arm 14. The blade connector 16 includes a pivot 38 or hinge connection between the blade connector 16 and locking arm 14, permitting the blade connector 16, and connected retractor blade 12, to be rotated in a generally upward and downward movement with respect to the locking arm 14 by the user. As previously stated, the blade connector 16 has a first aperture 32 formed in a generally central portion of the connector 16. The first aperture 32 extends through the blade connector 16 from a top portion 44 to the bottom portion 46, and is configured to receive the stem member 20 therein. In order to receive the stem member 20, the first aperture 32 has a generally cylindrical shape with a generally circular cross-section to receive the stem member 20 therein.

The blade connector 16 further includes one or more notches 34a, 34b provided about the outer edge of the first aperture 32. The notches 34a, 34b are configured to cooperatively receive the pin members 22 and 28 therein, to permit the rotator blade 12 to operate in both in a swivel or rotatable mode, with respect to the retractor arm 14. Similar to the first aperture 32, the notches 34a, 34b extend from the top surface 44 to the bottom surface 46 of the blade connector 16.

In the embodiment shown, dual notches 34a, 34b permit for slidable movement of the respective abutments 23a, 23b and 25a, 25b therein. The notches 34a, 34b are also configured to prevent rotatable movement of the stem member 20 once inserted in the first aperture 32 and the abutments 25a, 25b of the second pin member 28 are positioned in the respective notches 34a, 34b. In the embodiment illustrated, the second pin member 28 is positioned such that when the abutments 25a, 25b engage respective notches 34a, 34b, the retractor blade 12 may be locked with the outer surface 30 of the retractor blade 12 at approximately 90 degrees relative to the locking arm 14. Notably, by positioning the notches 34a, 34b, it is contemplated that the retractor blade 12, may be locked at any selected angle with respect to the locking arm 14.

As depicted, the blade connector 16 further includes a second aperture 60 formed generally along a sidewall 62 of the blade connector 16. The second aperture 60 extends from an outer wall 62, through the connector 16, and into communication with the first aperture 32. The second aperture 60 is configured to retain a control assembly 64 therein for selectively locking the stem member 20 vertically within the first aperture 32, when the retractor assembly 10 is in the locked mode, and for facilitating rotation of the stem member 20 of the retractor blade 12 in the unlocked swivel mode.

Figure 3A:
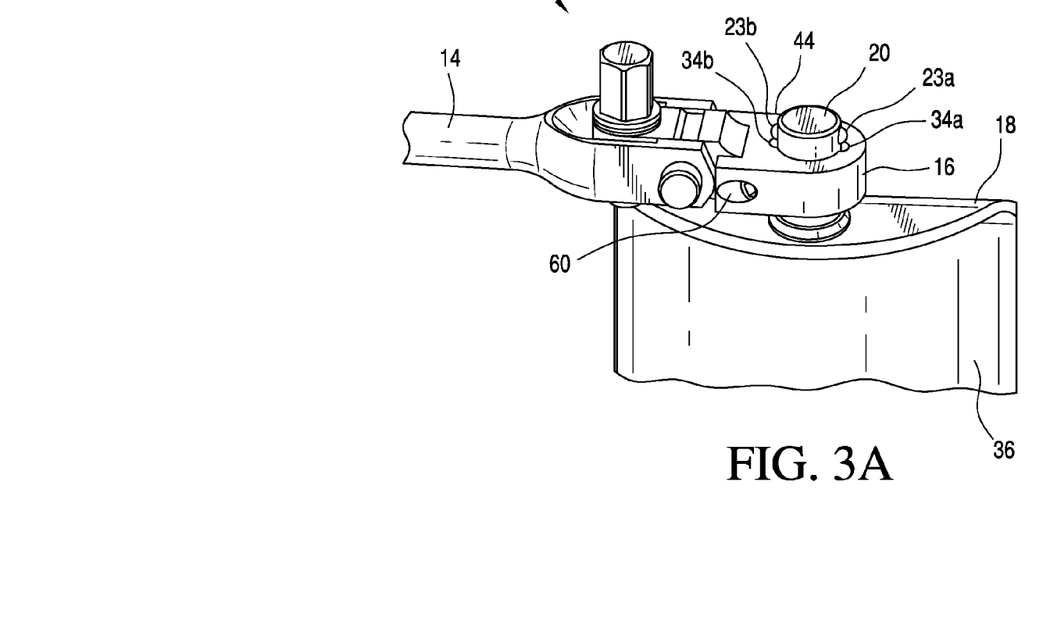
FIG. 3A is a top perspective view of the retractor blade assembly of FIG. 1, illustrating the blade connector and the retractor blade in an engaged position.
Figure 3B:
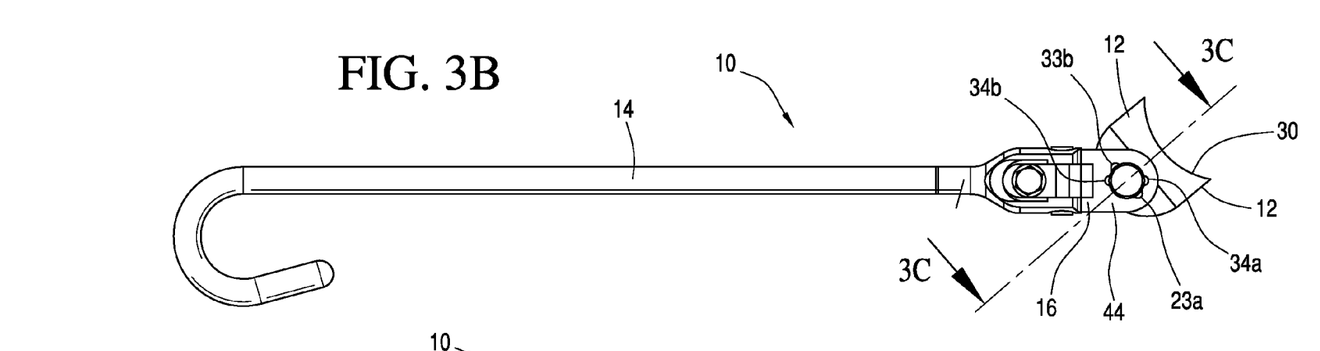
FIG. 3B is a top view of the retractor blade assembly of FIG. 1
Figures 3C, 4:
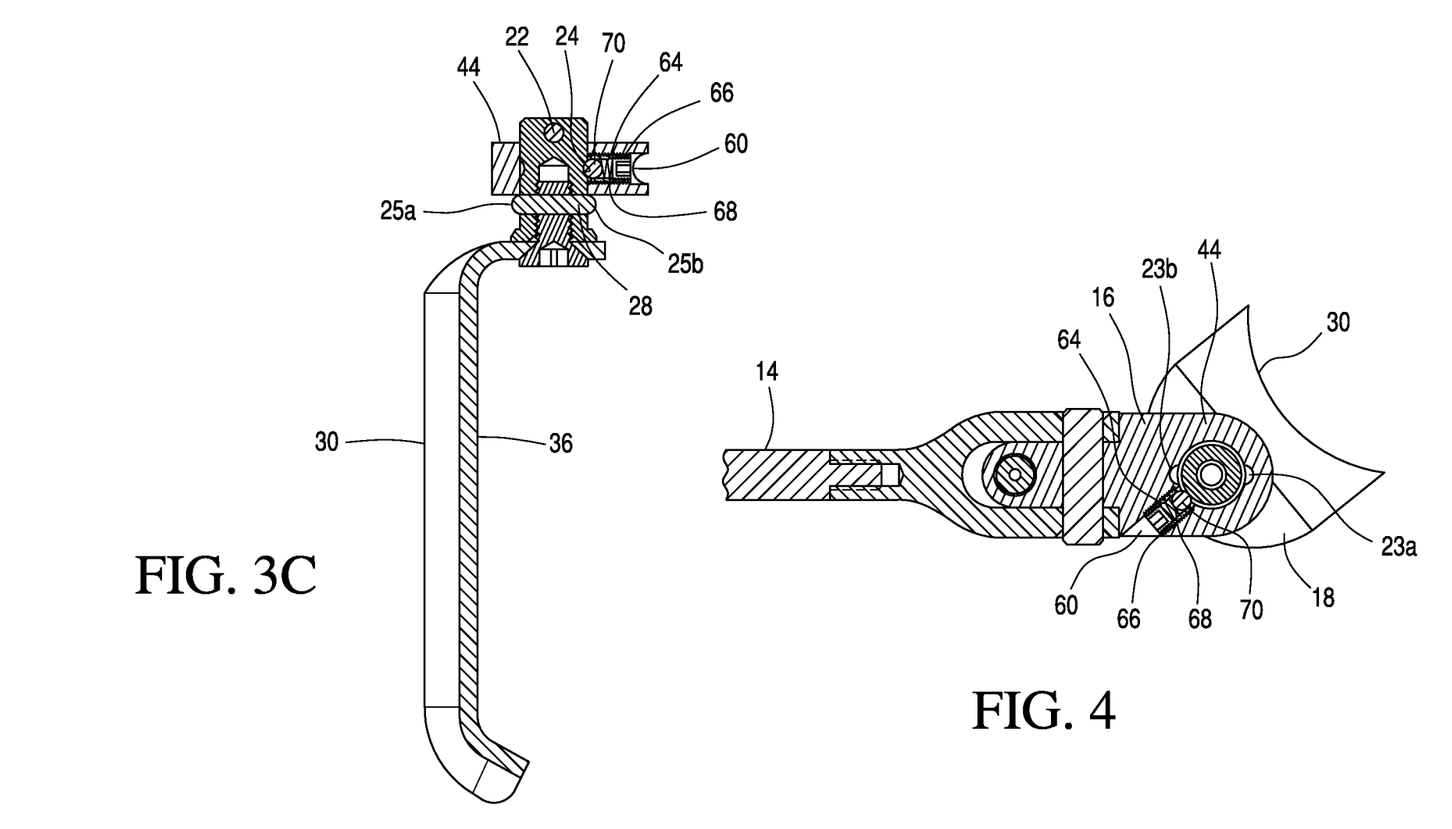
FIG. 3C is a side sectional view of the retractor assembly of FIG. 1, illustrating the blade connector and retractor blade connection.
FIG. 4 is a top sectional view of the retractor blade assembly of FIG. 1, in a swivel mode.
Figure 5:
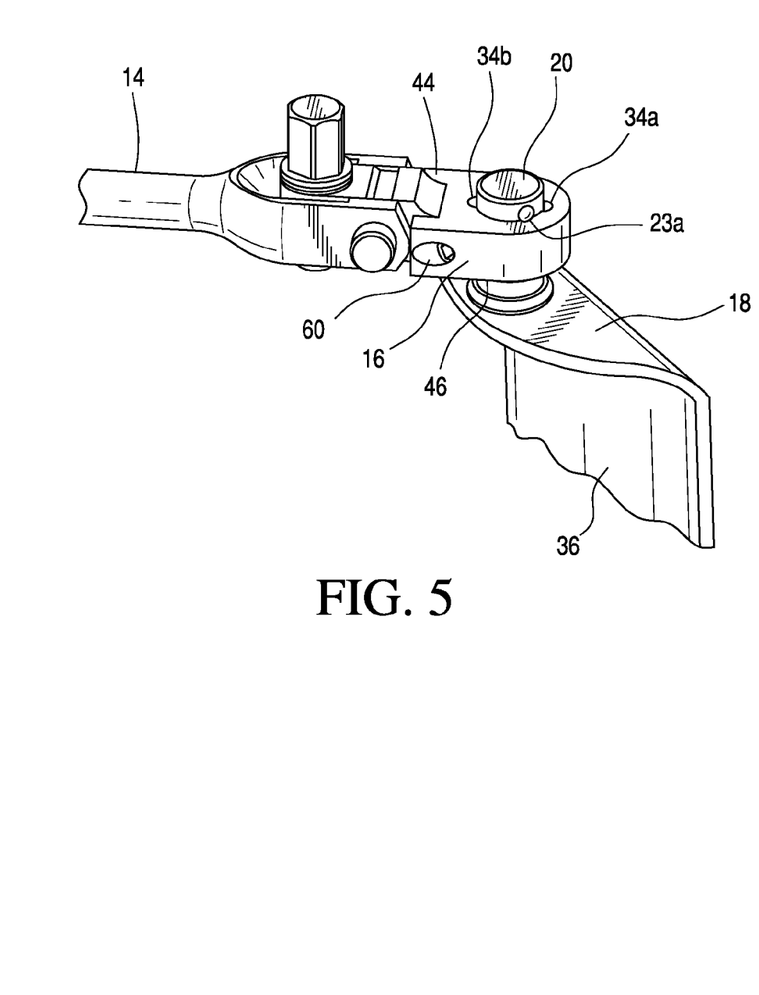
FIG. 5 is an elevational perspective view of the retractor blade assembly of FIG. 1, illustrating the retractor blade operatively connected to the retractor arm.
Figure 6:
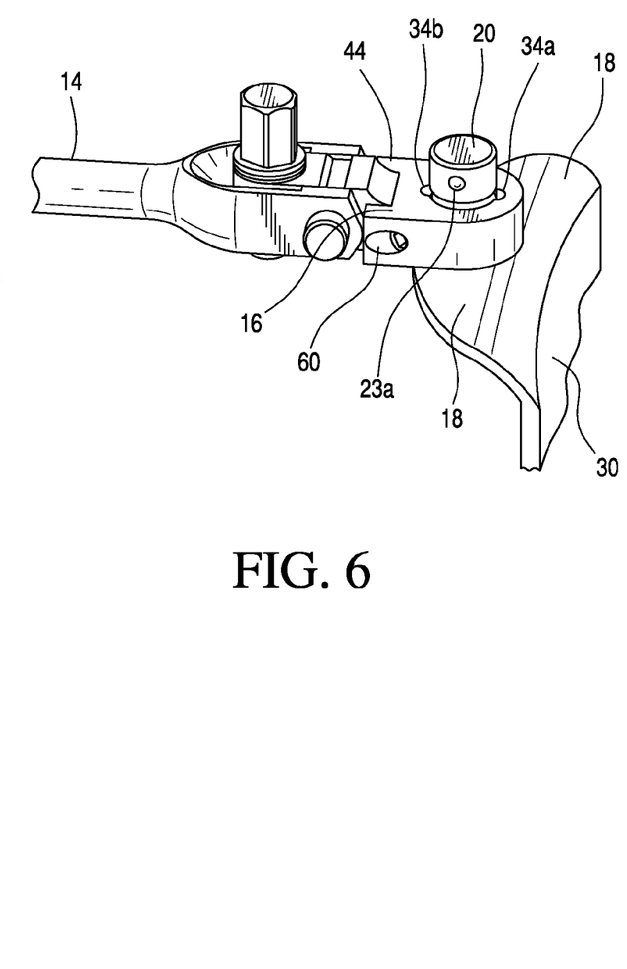
FIG. 6 is an elevational perspective view of the retractor blade assembly, illustrating the retractor blade, in a locked mode.
Figures 7, 8, 9:
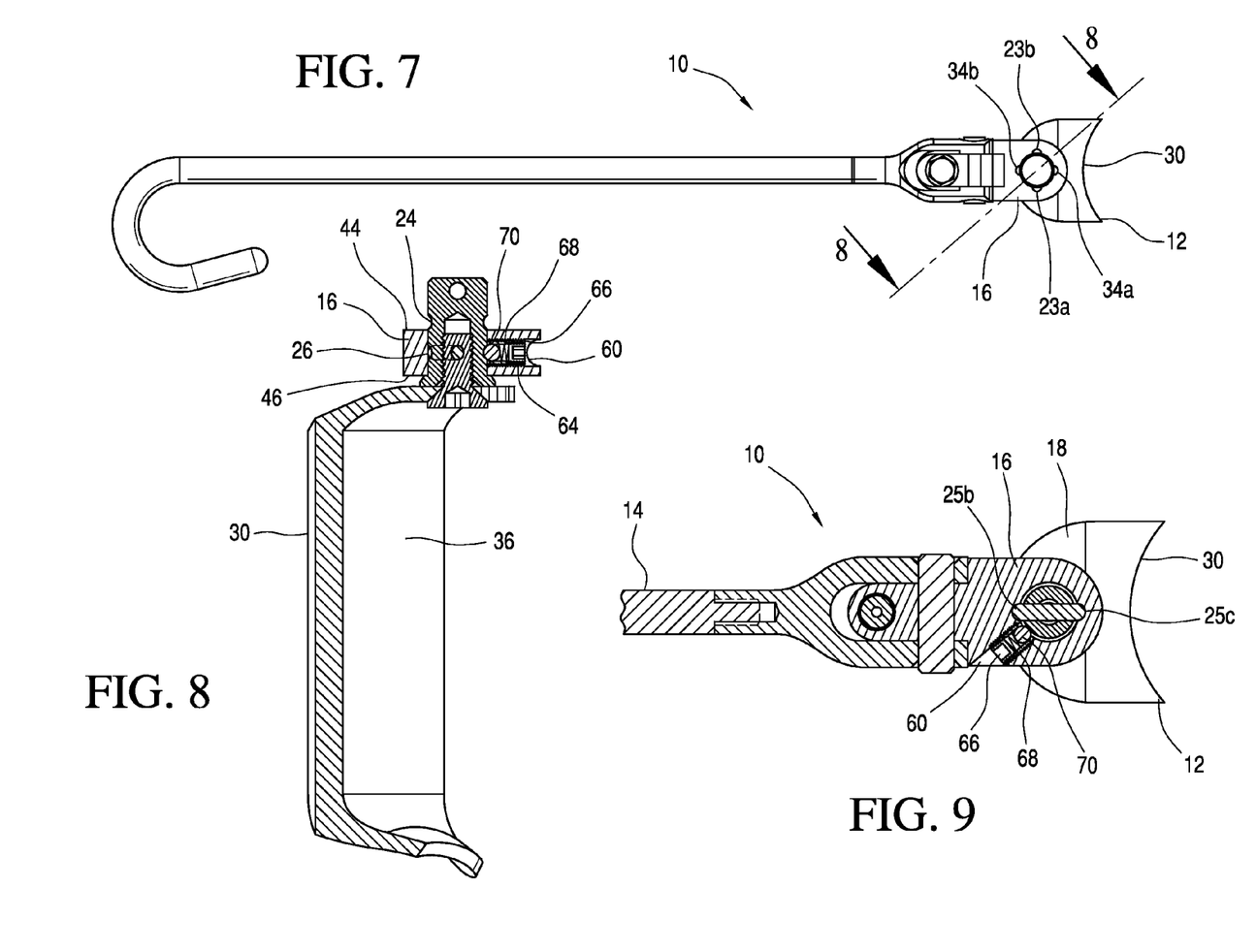
FIG. 7 is a top view of the retractor blade assembly of FIG. 6, in a locked mode.
FIG. 8 is a side sectional view of the retractor blade assembly of FIG. 6 in a locked mode.
FIG. 9 is a top sectional view of the retractor blade assembly of FIG. 6 in a locked mode.

As shown in FIGS. 3C and 8 the control assembly 64 generally includes a fastener 66 or adjustment member, a biasing member 68, such as a spring, for example, and a ball member 70. The control assembly 64, and specifically the ball member 70 engages the first groove 24 of the stem member 20 in a rotatable mode, and the second groove 26 in a locked mode.

To connect the retractor blade 12 to the locking arm 14, the retractor blade 12 is aligned with the blade connector 16, such that the stem member 20 is aligned with the first aperture 32. The stem member 20 is inserted vertically into the first aperture 32, such that the first pin member 22 is aligned with a first notch member 34a and second notch member 34b. The stem member 20 is slid through the first aperture 32 until the ball member 70 of the control assembly 64 is aligned with the first groove 24 and, the first pin member 22 is positioned generally above the surface 44 of the blade connector 16. As shown in 3C, in this configuration, the second pin member 28 is positioned below the connector 16, proximate to the lower surface 46 of the blade connector 16 and the control assembly 64 engages the first groove 24. As such, the ball member operatively engages the first groove 24, permitting the stem member 20, within the first aperture 20, to rotate or swivel the retractor blade 12 freely with respect to the retractor arm 14.

As shown in FIGS. 8 and 9, to lock the retractor blade 12 with the connector at a selected angle with respect to the retractor arm 14, the retractor blade 12 is swiveled such that the second pin member 26 and respective abutment 25a, 25b align with the respective notches 34a, 34b, permitting the stem member 20 to be moved vertically upward into the first aperture 20. As the abutments 25,25b engage the notches, the blade 12 is prevented from rotation, and is locked at a selected angle relative to the locking arm 14, which in this case is a 90 degree angle relative to the locking arm 14. Notably it is contemplated that the blade member and notch may be provided at any desired angle or at multiple angles, permitting the blade member to be locked at a selected angle.

In the inserted position, the retractor blade 12 is moved vertically until the ball member 70 engages the second groove 26 preventing further vertical movement upward and downward of the stem member 20 within the first aperture 20. The biasing member 68, and pressure applied by the ball member 70 on the second groove 26 may be adjusted by moving the adjustment fastener 66. To release the stem member 20 from the first aperture 20, the adjustable screw is engaged by the user, releasing pressure from the biasing member 68 acting on the ball member 70 and second groove 26.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A retractor blade assembly, comprising:
   an arm member;
   a retractor blade a having stem member provided at a top of the blade, the stem member including a first pin member, provided at an upper portion of the stem member, having at least one abutment extending outward from the stem member, a first groove provided below the first pin member, provided about the circumference of the stem member, a second groove provided below the first groove, provided about the circumference of the stem member, a second pin member having at least one abutment extending from the second groove,
   a blade connector including a body including a first aperture and at least one notch, both extending from a top surface of the body through a bottom surface of the body and configured to receive insertion of the stem member therein, the blade connector further including a second aperture extending from a side wall into an interior of the body in communication with the first aperture, and a locking assembly provided in the second aperture configured to selectively engage the first groove and the second groove of the stem member in an inserted position;

wherein when the stem member of the retractor blade is inserted in the first aperture in a first position, the locking assembly engages the first groove of the stem member, the first pin member is located above the top surface of the blade connector and the second pin member is located below the bottom surface of the blade connector, permitting the stem member and connected retractor blade to rotate, wherein when the stem member of the retractor blade is in a second position, the locking assembly engages the second groove of the stem member preventing vertical movement of the stem member, and at least one of the abutments of the second pin member is located in at least one of the notches of the blade connector, thereby locking the blade member in a locked position.

2. The retractor blade assembly of claim 1, wherein the stem member is moved vertically through the first aperture to move the retractor blade between the locked position and the rotatable position.

3. The retractor blade assembly of claim 1, wherein when the stem member is in an inserted position with the blade connector, the at least one abutment of the first pin member permits removal of the stem member from the blade connector when aligned with the at least one notch of the blade connector and prevents removal of the stem member when misaligned.

4. The retractor blade assembly of claim 1, wherein the at least one abutment of the first pin member and the at least one abutment of the second pin member are offset by approximately 90 degrees.

5. The retractor blade assembly of claim 1, wherein the locking assembly includes an adjustment screw and a ball member positioned to selectively engage the stem member.

6. The retractor blade assembly of claim 5, wherein the locking assembly further includes a biasing member in operative engagement with the adjustment screw and the ball member, such that movement of the adjustment screw controls movement of the ball member.

7. The retractor blade assembly of claim 6, wherein in the rotatable position, the ball member engages the first groove of the stem member facilitating rotatable movement of the retractor blade and in the locked position, the ball member engages the second groove of the stem member preventing vertical movement of the stem member relative to the blade connector.

8. The retractor blade assembly of claim 6, wherein the biasing member is a spring member.

9. The retractor blade assembly of claim 1, wherein the at least one abutment of the first pin member includes dual abutments and the at least one notch of the blade connector includes dual notches configured to receive the respective dual abutments.

10. The retractor blade assembly of claim 1, wherein the at least one abutment of second pin member includes dual abutments and the at least one notch of the blade connector includes dual notches extending therethrough and configured to receive the respective dual abutments of the second pin member.

11. The retractor blade assembly of claim 1, wherein in the locked position, at least one of the abutments of the second pin member and at least one of the notches of the blade connector are aligned such that an outer surface of the retractor blade is curved outward from the arm member.

12. A retractor blade assembly, comprising:
an arm member;
a retractor blade having outer edges which define a first plane and a stem member provided at a top of the blade, the stem member including a first pin member, provided at an upper portion of the stem member, the first pin member having at least one abutment extending outward from the stem member and parallel to the first plane, a first groove provided below the first pin member, provided about the circumference of the stem member, a second groove provided below the first groove, provided about the circumference of the stem member, a second pin member having at least one abutment extending from the second groove substantially perpendicular to the first plane,
a blade connector including a body including a first aperture and at least one notch, both extending from a top surface of the body through a bottom surface of the body and configured to receive insertion of the stem member therein, the blade connector further including a second aperture extending from a side wall into an interior of the body in communication with the first aperture, and a locking assembly provided in the second aperture configured to selectively engage the first groove and the second groove of the stem member in an inserted position;

wherein when the stem member of the retractor blade is inserted in the first aperture in a first position, the locking assembly engages the first groove of the stem member, the first pin member is located above the top surface of the blade connector and the second pin member is located below the bottom surface of the blade connector, permitting the stem member and connected retractor blade to rotate, wherein when the stem member of the retractor blade is in a second position, the locking assembly engages the second groove of the stem member preventing vertical movement of the stem member, and at least one of the abutments of the second pin member is located in at least one of the notches of the blade connector, thereby locking the blade member in a locked position.

13. The retractor blade assembly of claim 12, wherein the stem member is moved vertically through the first aperture to move the retractor blade between the locked position and the rotatable position.

14. The retractor blade assembly of claim 12, wherein when the stem member is in an inserted position with the blade connector, the at least one abutment of the first pin member permits removal of the stem member from the blade connector when aligned with the at least one notch of the blade connector and prevents removal of the stem member when misaligned with the at least one notch of the blade connector.

15. The retractor blade assembly of claim 12, wherein the at least one abutment of the first pin member and the at least one abutment of the second pin member are offset by approximately 90 degrees.

16. The retractor blade assembly of claim 12, wherein the locking assembly includes an adjustment screw and a ball member positioned to selectively engage the stem member.

17. The retractor blade assembly of claim 16, wherein the locking assembly further includes a biasing member in operative engagement with the adjustment screw and the ball member, such that movement of the adjustment screw controls movement of the ball member.

18. The retractor blade assembly of claim 17, wherein in the rotatable position, the ball member engages the first groove of the stem member facilitating rotatable movement of the retractor blade and in the locked position, the ball member engages the second groove of the stem member preventing vertical movement of the stem member relative to the blade connector.

19. The retractor blade assembly of claim 17, wherein the biasing member is a spring member.

20. The retractor blade assembly of claim 12, wherein the at least one abutment of the first pin member includes dual abutments and the at least one notch of the blade connector includes dual notches configured to receive the respective dual abutments.

\* \* \* \* \*